(12) United States Patent
Hubbell et al.

(10) Patent No.: US 6,405,588 B1
(45) Date of Patent: Jun. 18, 2002

(54) MONITORING WELL

(75) Inventors: Joel M. Hubbell; James B. Sisson, both of Idaho Falls, ID (US)

(73) Assignee: Bechtel BWXT Idaho, LLC, Idaho Falls, ID (US)

( * ) Notice: Subject to any disclaimer, the term of this patent is extended or adjusted under 35 U.S.C. 154(b) by 0 days.

(21) Appl. No.: 09/707,489

(22) Filed: Nov. 5, 2000

(51) Int. Cl.⁷ .......................... E21B 44/00; E21B 43/00; G01N 25/56
(52) U.S. Cl. .......................... 73/152.46; 73/73; 166/53; 166/113
(58) Field of Search .................... 73/152.46, 152.29, 73/152.51, 73, 863.71; 166/53, 113

(56) References Cited

U.S. PATENT DOCUMENTS

| | | | |
|---|---|---|---|
| 5,481,927 A | * | 1/1996 | Hubbell et al. ........... 73/863.71 |
| 5,520,248 A | * | 5/1996 | Sisson et al. ........... 166/250.02 |
| 5,553,492 A | * | 9/1996 | Barrett et al. ............. 73/152.29 |
| 5,644,947 A | * | 7/1997 | Hubbell et al. ................. 73/73 |
| 5,758,538 A | * | 6/1998 | Hubbell et al. ................. 73/73 |
| 5,878,646 A | * | 3/1999 | Schewe ..................... 91/376 R |
| 5,906,238 A | * | 5/1999 | Carmody et al. .............. 166/53 |
| 5,915,476 A | * | 6/1999 | Hubbell et al. .............. 166/113 |
| 5,969,242 A | * | 10/1999 | Hubbell et al. .......... 73/152.51 |

* cited by examiner

Primary Examiner—Hezron Williams
Assistant Examiner—J L Politzer
(74) Attorney, Agent, or Firm—Wells, St. John, Roberts Gregory & Matkin

(57) ABSTRACT

The present invention relates to a monitoring well which includes an enclosure defining a cavity and a water reservoir enclosed within the cavity and wherein the reservoir has an inlet and an outlet. The monitoring well further includes a porous housing borne by the enclosure and which defines a fluid chamber which is oriented in fluid communication with the outlet of the reservoir, and wherein the porous housing is positioned in an earthen soil location below-grade. A geophysical monitoring device is provided and mounted in sensing relation relative to the fluid chamber of the porous housing; and a coupler is selectively moveable relative to the outlet of reservoir to couple the porous housing and water reservoir in fluid communication. An actuator is coupled in force transmitting relation relative to the coupler to selectively position the coupler in a location to allow fluid communication between the reservoir and the fluid chamber defined by the porous housing.

27 Claims, 5 Drawing Sheets

MONITORING WELL

TECHNICAL FIELD

This invention relates to monitoring wells, and more specifically to monitoring wells used for determining soil conditions within below-grade earthen soil.

CONTRACTUAL ORIGIN OF THE INVENTION

This invention was made with United States Government support under Contract No. DE-AC07-94ID13223, now Contract No. DE-AC07-99ID13727 awarded by the United States Department of Energy. The United States Government has certain rights in the invention.

BACKGROUND OF THE INVENTION

Various devices have been designed and manufactured over time and which are is useful when used in an earthen profile to determine or calculate hydraulic gradients. These hydraulic gradients have been employed to determine the direction of water movement and to estimate water flux using unsaturated hydraulic conductivity. As should be understood, the movement of water in an unsaturated earthen zone is important for engineering studies, hazardous waste site monitoring, recharge studies and irrigation management practices. For example, if the moisture potential of soil can be accurately monitored, irrigation can be controlled to optimize the rate of plant growth.

One type of instrument used heretofore for measuring soil moisture potential is the tensiometer. A conventional tensiometer comprises a sealed tube defining a chamber which is normally completely filled with water; a hollow porous tip on one end of the tube; and a vacuum gauge connected to the water chamber. The porous tip is inserted in the soil and establishes hydraulic contact between the water in the tube and the moisture in the soil surrounding the tip. Relatively dry soil tends to withdraw water from the tube through the porous tip. However, since the tube is sealed, only a minute amount of water is actually withdrawn. Accordingly, the water in the tube is placed under tension by this effect of the dry soil, thus creating a measurable sub-atmospheric pressure in the tube. Higher moisture contents in the soil produce correspondingly less vacuum in the tube, and completely saturated soils register substantially zero vacuum or atmospheric pressure.

Typical tensiometer constructions provide a tube or column of water which extends from the porous tip to above grade. It will be apparent that the deeper the porous tip is buried, the longer the column of liquid above it will become.

Air presence in the water reservoir during tensiometric measurement is undesirable. In this regard, air can enter the reservoir by diffusing through the porous tip. More commonly, dissolved air present in water that enters the vessel comes out of solution in the reduced pressure environment of the tensiometer. In this situation, if left unchecked, the entire tensiometer would eventually become filled with air. This entrapped air will increase the time required to reach pressure equilibrium because large volumes of water must move through the porous tip to effect the mass transfer of air through the tip. Thus, in order to obtain accurate measurements of relative soil moisture, the air is desirably purged from the tensiometer reservoir and replaced with water.

Accordingly, manually operated de-airing systems have been designed for conventional tensiometers. However, such designs are inadequate for use with tensiometers monitoring soil moisture potential deep within below-grade earthen soil. Furthermore, one of the most costly aspects of using tensiometers in the field is the periodic maintenance schedule needed to routinely purge the air from the reservoir.

Accordingly, there remains a need for a method of monitoring soil moisture potential deep within below-grade earthen soil, and to devices which facilitate such measurements. Although a principal motivation for this invention arose from concerns associated with deep soil use of tensiometers, the artisan will recognize other uses of the invention which is only intended to be limited by the accompanying claims appropriately interpreted in accordance with the Doctrine of Equivalents.

BRIEF DESCRIPTION OF THE DRAWINGS

Preferred embodiments of the invention are described below with reference to the following accompanying drawings.

OBJECTS AND SUMMARY OF INVENTION

Figure 1:
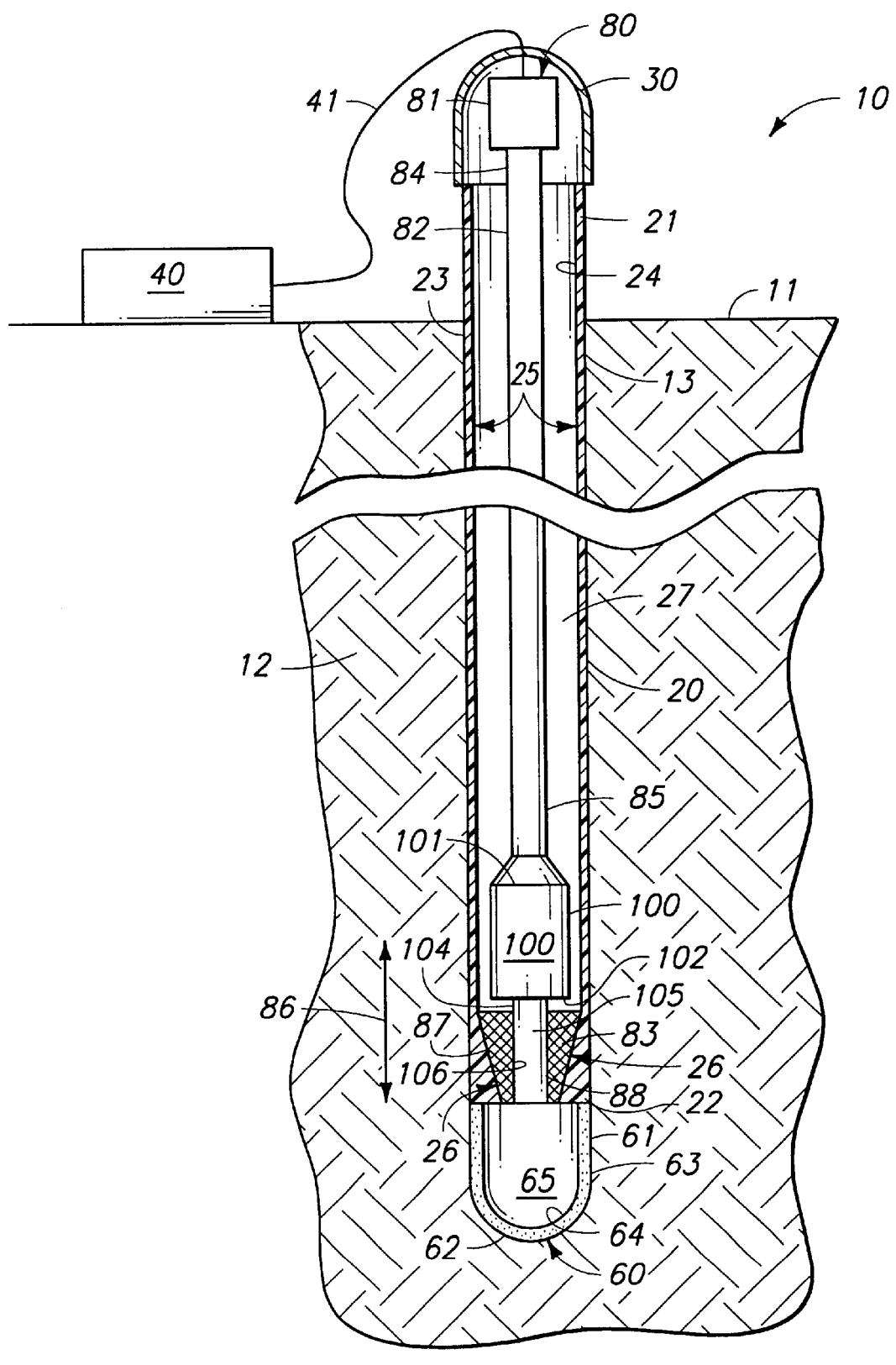
FIG. 1 is a longitudinal, vertical, sectional view of one form of a monitoring well of the present invention.

Therefore, one aspect of the present invention is to provide an improved monitoring well for evaluating and monitoring soil moisture potential within below-grade earthen soil.

Another aspect of the present invention is to provide a monitoring well which includes a housing defining a cavity which, in one form of the invention, includes a porous receptacle borne by the housing. The porous receptacle defines a fluid chamber disposed in fluid communication with the cavity. The monitoring well further includes a geophysical monitoring device disposed in sensing relation relative to the fluid chamber of the porous receptacle, and an actuator for selectively inhibiting fluid communication between the porous receptacle and cavity.

Another aspect of the present invention is to provide a monitoring well which, in one form of the invention, includes an antenna extending from the housing, and data transmission circuitry operatively coupling the antenna to the geophysical monitoring device, and wherein data generated by the geophysical monitoring device is transmitted by the antenna to a remote location.

Another aspect of the present invention is to provide a monitoring well which, in one form of the invention, includes a microcontroller operatively coupled to each of a geophysical monitoring device; a transmitter; and an actuator. The monitoring well further includes an electrical storage device operatively coupled to the microcontroller and the related data transmission circuitry.

Another aspect of the present invention is to provide a monitoring well which, in one form of the invention, includes an aperture defined by the housing and which provides fluid communication between the porous receptacle and the cavity. Still further, the invention includes a sealing member disposed in force receiving relation relative to the actuator, and wherein the actuator selectively moves the sealing member along a path of travel between a first and a second position.

Another aspect of the present invention is to provide a monitoring well which, in one form of the invention, includes an actuator having a motor, a drive member, and gear structures, and wherein the gear structures are operatively coupled between the motor and the drive member, and wherein the drive member is disposed in force receiving relation relative to the motor, and wherein the drive member has a terminal end, and wherein energizing the motor causes the substantially reciprocal movement of the terminal end of the drive member, and wherein the movement of the terminal end selectively inhibits fluid communication between the porous receptacle and the cavity.

Another aspect of the present invention is to provide a monitoring well which, in one form of the invention, includes an enclosure defining a cavity, and a water reservoir is enclosed within the cavity, and wherein the reservoir has an inlet and an outlet. The monitoring well further comprises a porous housing borne by the enclosure, and which defines a fluid chamber which is oriented in fluid communication with the outlet of the reservoir, and wherein the porous housing is positioned in an earthen soil location below-grade. The monitoring well further comprises a geophysical monitoring device mounted in sensing relation relative to the fluid chamber of the porous housing and a coupler selectively moveable relative to the outlet of the reservoir to couple the porous housing and water reservoir in fluid communication. An actuator is provided and is coupled in force transmitting relation relative to the coupler to selectively position the coupler in a predetermined location to allow fluid communication between the reservoir and the fluid chamber defined by the porous housing.

DETAILED DESCRIPTION OF THE PREFERRED EMBODIMENTS

This disclosure of the invention is submitted in furtherance of the constitutional purposes of the U.S. Patent Laws "to promote the progress of science and useful arts" (Article 1, Section 8).

Referring now to FIG. 1, a monitoring well in accordance with one aspect of the invention is generally indicated by the numeral 10. The monitoring well 10 of the subject invention is buried below the surface of the earth 11 in a below-grade portion 12. A bore hole 13 of suitable dimensions receives the monitoring well 10. The monitoring well 10 includes a housing, enclosure or conduit 20, which is received in the bore hole 13 and which has proximal end 21, and an opposite, distal end 22. As will be recognized in this embodiment of the invention, the conduit 20 is substantially uniformly linear, and the proximal end 21 extends above the earth's surface or above-grade 11, thereby allowing convenient access to same. Further, the conduit 20 is oriented in a substantially non-horizontal orientation relative to the surface of the earth 11. In particular, the conduit 20 is oriented in such a fashion that the distal end 22 is located at a lower relative elevation with respect to the proximal end 21. The conduit 20 has an outside surface 23, and an inside surface 24 which defines a cavity, or passageway 27 therein. The inside surface 24, at the proximal end 21, defines a substantially cylindrically shaped surface having an inside diametral dimension 25 that extends to the distal end 22. The inside surface of the distal end 22 of conduit 20 defines a substantially frustoconical shaped surface 26. The largest diametral dimension of the frustoconical shaped surface 26 is located in spaced relation relative to the distal end 22 and the smallest diametral dimension of the frustoconical shaped surface is located adjacent the distal end 22.

A surface cap 30 releasably engages the proximal end 21. A data logging device 40 of conventional design is positioned remotely relative to the monitoring well 10 and includes an electrical conduit 41 which is received through the surface cap 30 and is electrically coupled with an actuator which will be discussed in greater detail hereinafter.

Figure 7:
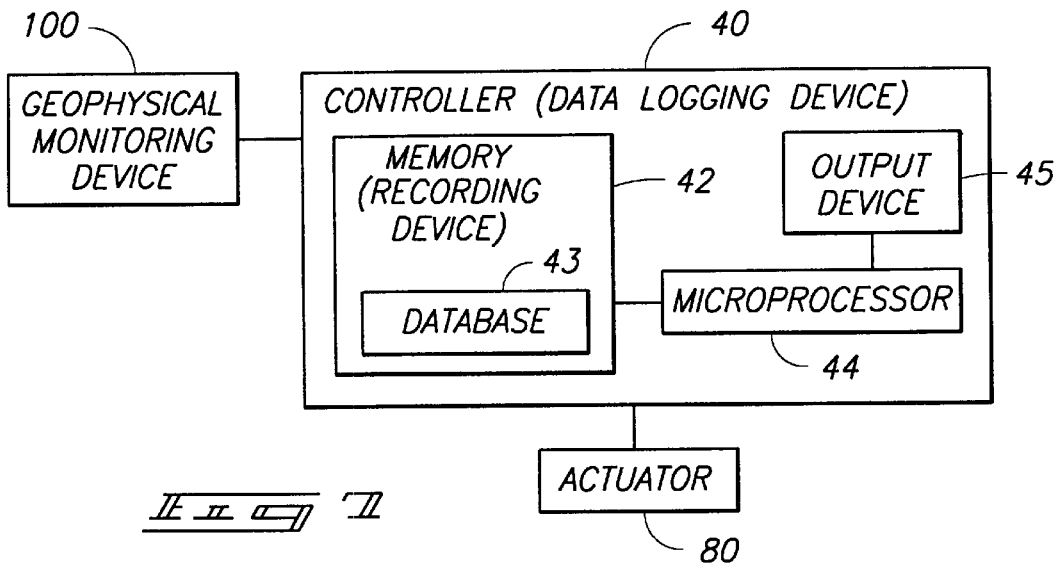
FIG. 7 is a block diagram of a controller coupled to a geophysical monitoring device and actuator, in accordance with the present invention.

As best seen by reference to FIG. 7, the data logging device 40 or controller comprises a microprocessor 44 which is electrically coupled to an output device 45 and a memory 42, and/or recording device, and which may also include a database 43. The controller 40 is coupled in signal transmitting and receiving relation relative to the actuator, and a geophysical monitoring device which will be described in more detail hereinafter.

Referring again to FIG. 1, a porous housing or receptacle 60 is mounted on conduit at the distal end 22, and extends substantially, longitudinally outwardly from the distal end 22 adjacent the smallest diametral dimension of the frustoconically shaped surface 26. The porous housing 60 comprises a ceramic cup of conventional design and which is well known to those skilled in the art. The porous housing 60 permits the movement of fluids into and out of same. The porous housing 60 has a first end 61, and an opposite second end 62. Further, the porous housing as an outside surface 63, which defines an outside diametral dimension. The porous housing 60 further has an inside facing surface 64 which defines a fluid chamber 65. The frustoconically shaped surface defines an outlet 26 between the cavity 27 and the fluid chamber 65, thus providing fluid communication therebetween. The porous housing 60 is secured in place by a suitable fastening means such as by adhesives, thread fasteners, and the like. It should be understood that the porous housing 60 could be secured to the conduit 20 by a separate, discrete member or adapter (not shown) defining inside diametral dimensions having the frustoconical surface 26, or outlet, similar to the distal end 22 of conduit 20 shown in FIG. 1.

The monitoring well 10 of the present invention includes an actuator which is generally designated by the numeral 80. As illustrated in FIG. 1, this embodiment of the present invention provides an actuator 80 having a driving device 81, a drive member 82, a geophysical monitoring device (which will be discussed below), and a coupler or sealing member 83. The driving device 81 is housed within the surface cap 30, and secured therein, and is represented in FIG. 1 by a simple box. The driving device 81 normally comprises a linear actuator which will be more thoroughly discussed hereinafter. The drive member 82 comprises a substantially linear arm, or tube, which is telescopically received within the conduit 20, and is rendered substantially reciprocally moveable within the cavity 27. The drive member 82 has a proximal end 84, and an opposite, distal end 85. The proximal end 84 of the drive member 82 is mounted in force receiving relation relative the driving device 81. Further, the distal end 85 of drive member 82 is secured to a geophysical monitoring device 100. This geophysical monitoring device normally comprises a pressure transducer. The transducer 100 has a is first end 101, which is secured to the distal end 85 of drive member 82, and an opposite, second end 102. The second end 102 of transducer 100 has a cylindrical tube 104 extending substantially longitudinally, outwardly therefrom and which defines a passageway 105. The passageway 105 provides fluid communication between the transducer 100 and the fluid chamber 65 which is defined by the porous housing 60. Tube 104 has an exterior surface 106 having a given diametral dimension. It should be understood that the actuator 80 may not include the geophysical monitoring device 100. The geophysical monitoring device 100 could be positioned in any sensing location relationship relative the porous housing 60. It should also be understood that the monitoring well 10 of the present invention is operable to work in combination with various other geophysical monitoring devices which are operable to determine other below-grade parameters of interest.

The sealing member 83 defines a substantially centrally located, and longitudinally extending channel 88 which has a diametral dimension which is slightly larger than the outside diametral dimension of tube 104 to allow the channel 88 to be received over the tube 104. The sealing member 83 defines an exterior wall 87 which is frustoconically shaped for complementary sealing mating relationship with respect to the frustoconically shaped surface 26. An exemplary suitable sealing member material is resilient and may comprise any number of synthetic polymeric based material. It should be understood that other configurations of sealing member 83 could be used, for example, an o-ring or solid round plate secured on the distal end 85 of the actuator 80 for complementary sealing mating relationship with respect to an inwardly, laterally, extending shelf (not shown) defined by the inside surface 24 of the conduit 20. An exemplary o-ring or round plate configuration may comprise a valve design. Additionally, any combination of these exemplary alternatives could also be used as a sealing member, for example, an o-ring in combination with a round plate.

It should be understood that as the driving device 81 is energized, the drive member 82 is operable to cause substantially reciprocal movement of the sealing member 83. In this regard, the sealing member 83 moves along a substantially reciprocal path of travel 86 between a first position and a second position. The first position is defined as an occluding position wherein the sealing member 83 rests in sealing engagement against the frustoconical surface 26 to inhibit or impede fluid communication between the cavity 27 and fluid chamber 65 of porous housing 60. The second position is defined when the sealing member 83 is positioned remotely or in spaced relation relative to the frustoconical surface 26 to provide fluid communication between the cavity 27 and fluid chamber 65 of porous housing 60. It should be understood that while the sealing member 83 of FIG. 1 is substantially frustoconically shaped, it is conceivable that other shapes can provide the releasable fluid sealing engagement of the geophysical, or hydro-geological monitoring device with equal success. For example, a valve (not shown) driven by an actuator could move to abut a circular ledge (not shown) within a cavity of a monitoring well thereby providing the fluid sealing engagement.

Figure 2:
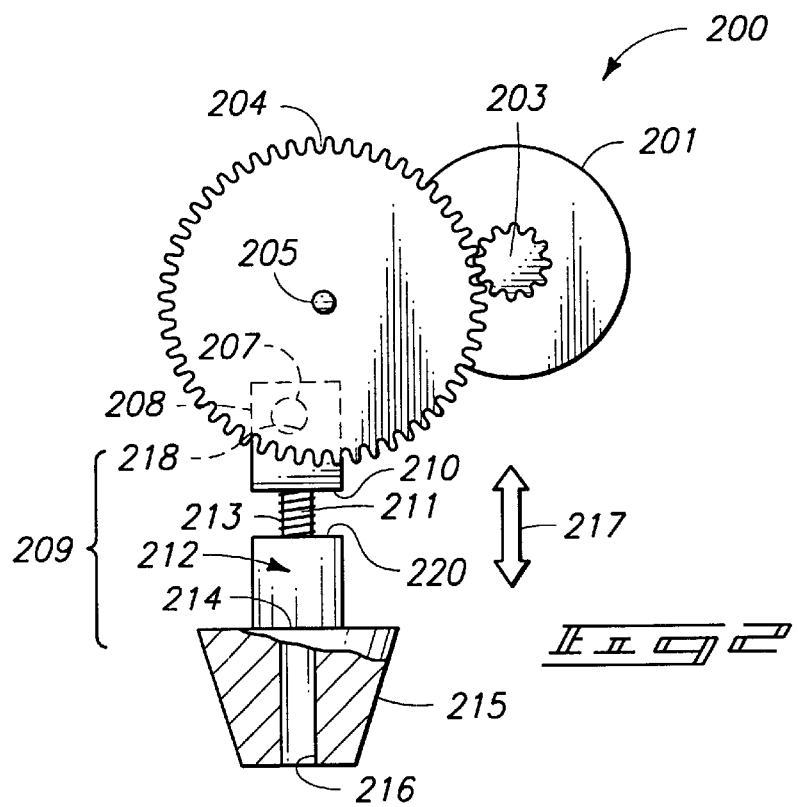
FIG. 2 is a partial, side elevation view of an actuator employed with one form of the present invention.
Figure 3:
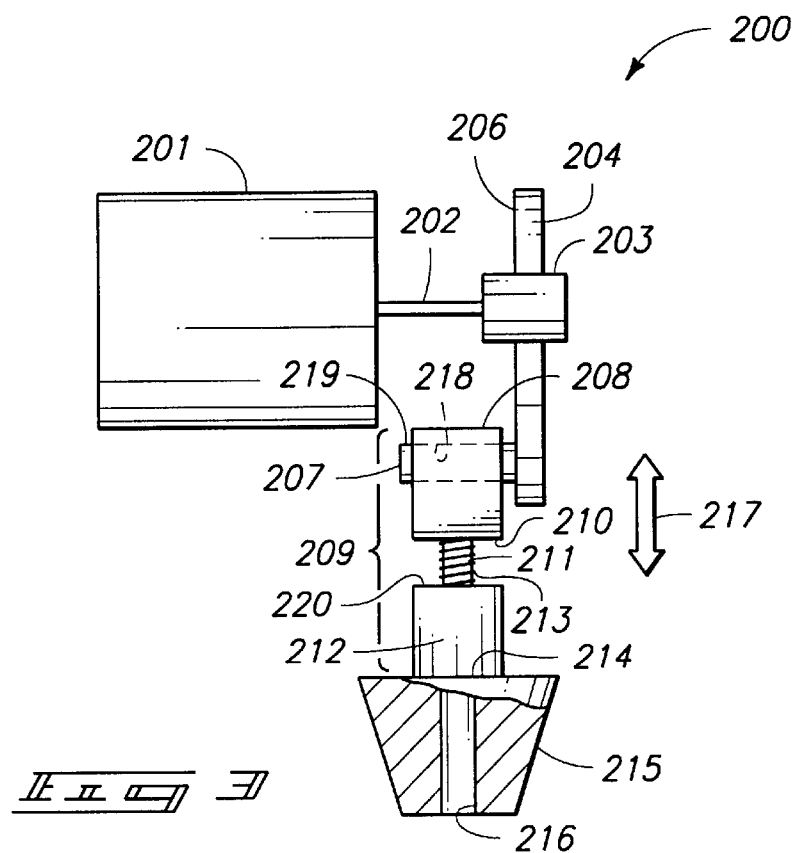
FIG. 3 is a partial, front elevation view of that shown in FIG. 2.

As best seen by reference to FIGS. 2 and 3, an exemplary actuator is illustrated and indicated generally by reference numeral 200. Actuator 200 comprises a motor 201 for the driving device. A drive shaft 202 extends laterally from motor 201. The drive shaft 202 comprises a first end which is located opposite the motor 201, and which has a pinion 203 affixed thereon. Pinion 203 meshes with a gear 204. As best seen in FIG. 2, the gear 204 is rotatably supported on a centrally located pivot 205. While not shown, those skilled in the art will understand that pivot 205 may have at least one end, and preferably two opposed ends which are rotatably mounted or otherwise supported within the monitoring well 10. Gear 204 has a rearwardly facing wall 206 which defines an aperture (not shown), and which is spaced from the pivot 205 to receive and secure a linear connecting rod 207. The connecting rod 207 has a portion 219 which extends substantially perpendicularly from the rearwardly facing wall 206. A drive member 209 is provided and comprises a first body 208 defining a channel 218 which receives and transversely secures the portion 219 of the connecting rod 207. The first body 208 further comprises a lower end portion 210. Drive member 209 further comprises a second body 212 having an upper end portion 220 which faces lower end portion 210 of the first body 208. A strut rod 211 slidingly engages the first body 208 through lower end portion 210, and engages the second body 212 through upper end portion 220. This arrangement permits reciprocal substantially telescopic motion of one body relative to the other body. A biasing spring 213 is received about the strut rod 211 and abuts against the lower end portion 210 and upper end portion 220 of first and second bodies 208 and 212, respectively. As seen from a study of FIGS. 2 and 3, the biasing spring 213 imparts a force to urge the bodies 208 and 212 apart. Second body 212 further comprises a lower end 214 opposite the upper end 200. The lower end 214 supports a sealing member 215 of construction similar to the sealing member 83 of FIG. 1. The sealing member 215 defines a passageway 216. It should be understood that the second portion 212 could comprise a linear arm, or drive member similar to the construction of drive member 82 of FIG. 1, including the transducer. In operation, the pinion 203 and gear 204 are operatively coupled between the motor 201 and the drive member 209. Further, the drive member 209 and the sealing member 215 are disposed in force receiving relation relative to the motor 201. As will be seen, energizing the motor 201 results in substantially reciprocal movement 217 of the sealing member 215 to selectively inhibit fluid communication between the porous housing (shown in FIG. 1) and the cavity or conduit (shown in FIG. 1).

Figure 4:
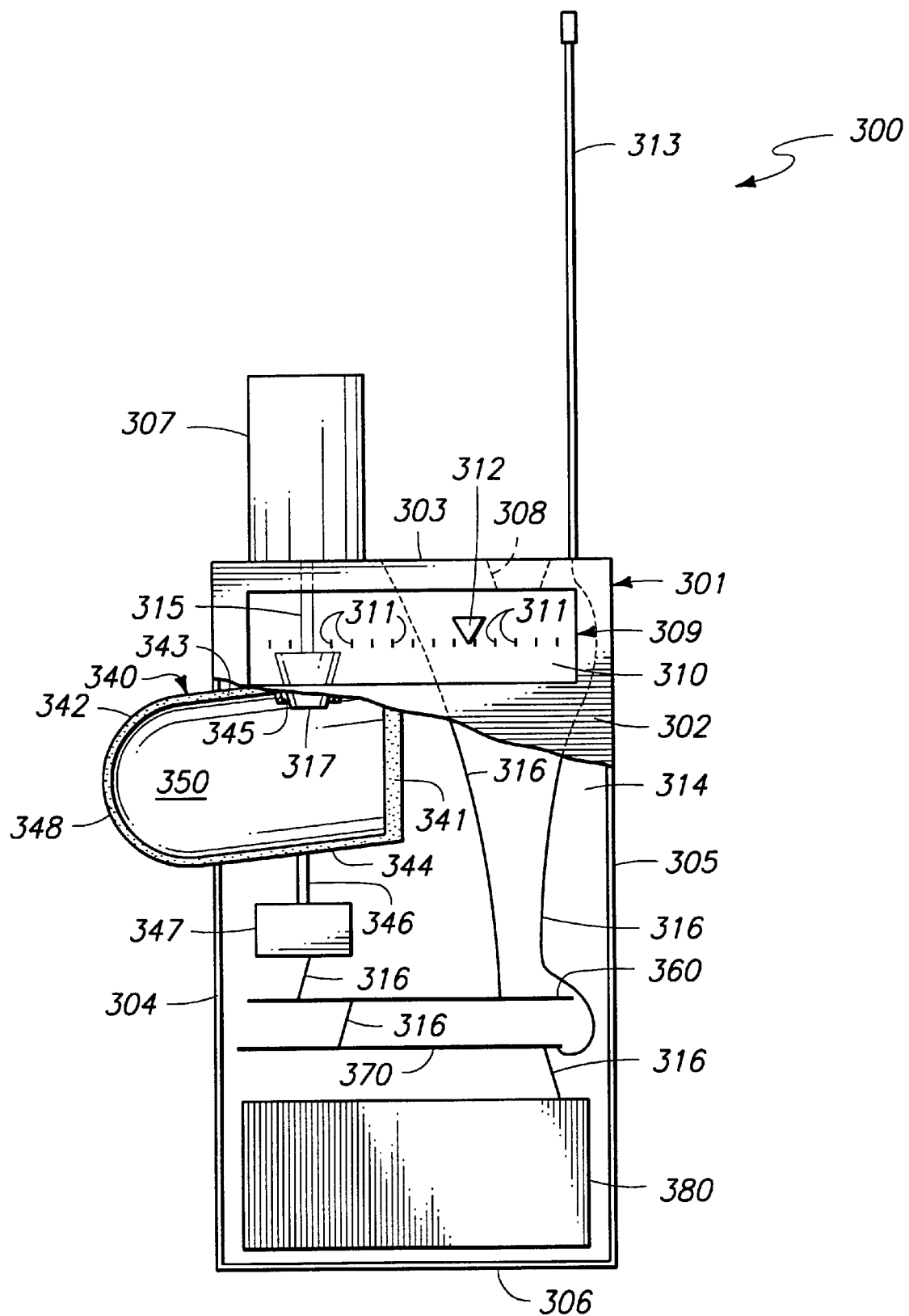
FIG. 4 is a fragmentary, longitudinal, vertical, sectional view of a second form of the present invention.
Figure 5:
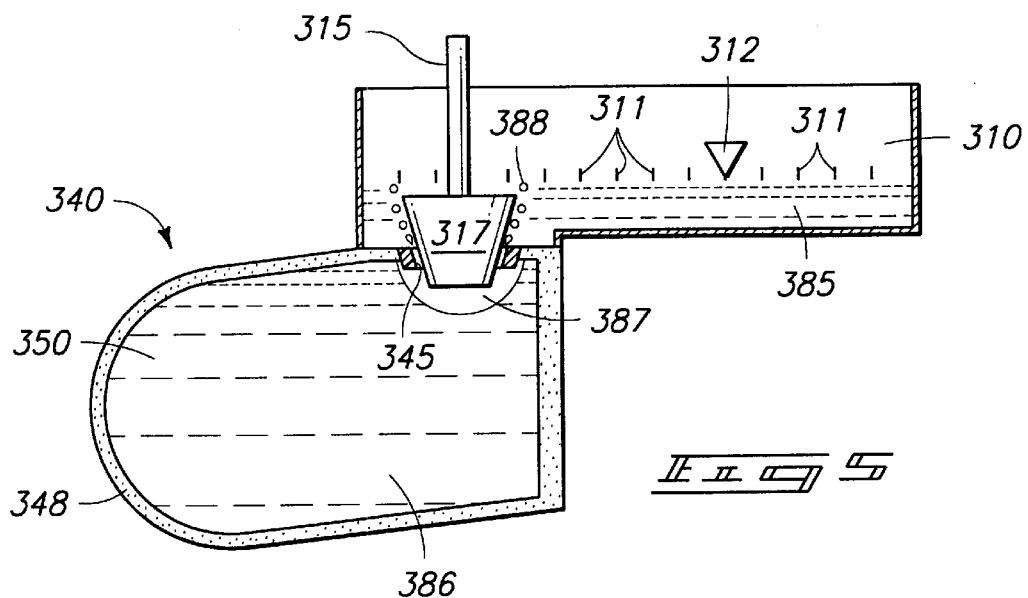
FIG. 5 is a partial, enlarged, longitudinal sectional view of a reservoir and porous housing shown in FIG. 4.
Figure 6:
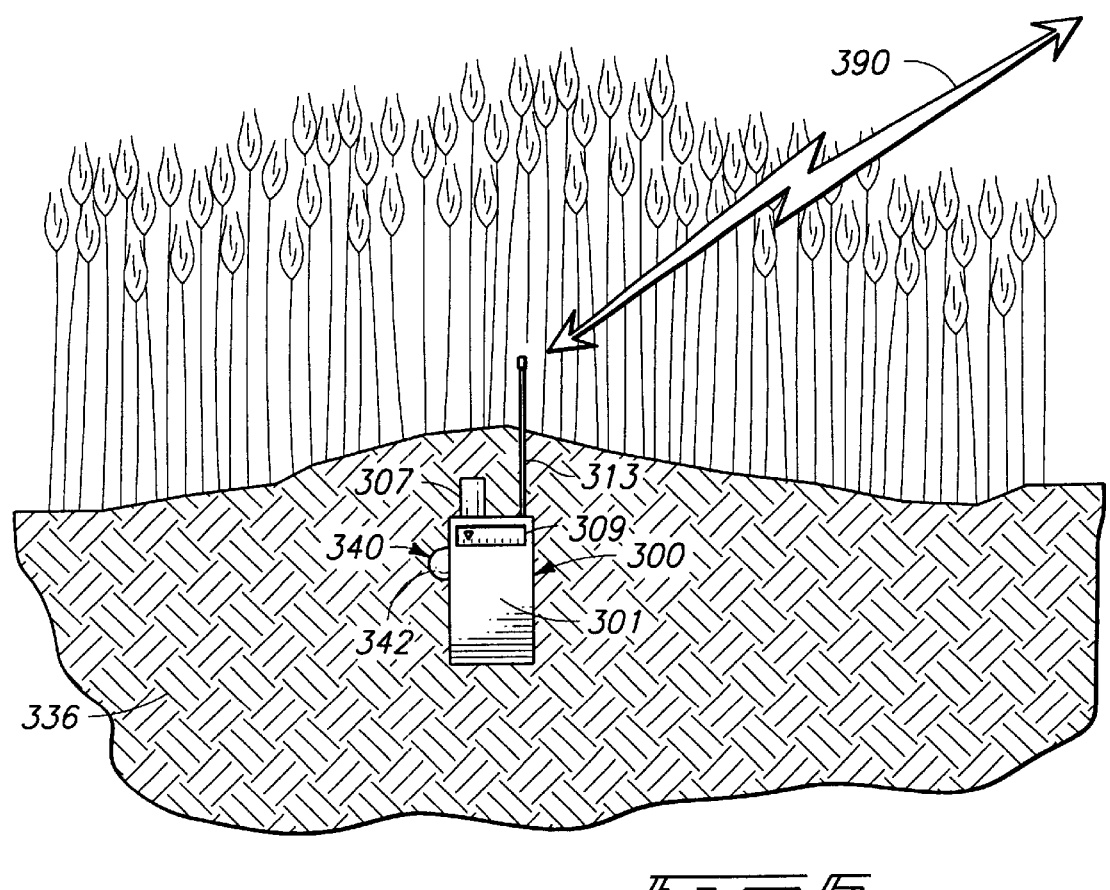
FIG. 6 is a diagrammatic, environmental view of the second form of the invention.

As best seen by reference to FIGS. 4–6, a second embodiment of a monitoring well is generally indicated by the numeral 300. The monitoring well 300 comprises a housing 301 which defines a generally rectangularly shaped box or enclosure that includes a front surface 302; a top surface 303; left surface 304; right surface 305; bottom surface 306; and back surface not shown. Top surface 303 includes an outer casing 307 which extends substantially normally upwardly and is proximate to the left surface 304. The outer casing 307 protects at least a portion of an actuator, for example, a driving device (not shown) from the environment. A drive member 315, for example a linear drive arm, extends downwardly from the outer casing 307 into the housing 301 and is connected to a resilient sealing member 317. Resilient sealing member 317 is substantially frustoconically shaped. It is understood that the drive member 315 is disposed in force receiving relation relative the driving device for alternative reciprocal motion generally along a longitudinal axis of the drive member 315. Top surface 303 further supports an antenna 313 which extends normally upwardly and is proximately located relative to the right surface 305. Between the outer casing 307 and antenna 313, top surface 303 defines an aperture 308 which permits access into the housing 301. A portion of front surface 302 which is adjacent the top surface 303 supports a rectangular window 309. The window which comprises, for example, glass permits viewing into at least a portion of a reservoir 310 which is located within the housing 301. Reservoir 310 is selectively fluidly sealed within the housing 301 and stores a fluid, for example water (best seen in FIG. 5 and described subsequently). Aperture 308 provides selective fluid communication between the reservoir 310 and the ambient environment. It should be understood that aperture 308 is sealed to prevent contamination from the environment by a conventional method such by utilizing resilient synthetic substances such as a plastic top (not shown) and which is secured in occluding relation relative to the aperture 308, by complementary threads (not shown). The rectangular window 309 includes water level marks 311 and an indicator 312 for permitting visual monitoring of the water level. The configuration and operation of the water level marks 311 and indicator 312 are understood by one skilled in the art. These may include, for example, a mechanical float mechanism or an electronic mechanism. It should be understood that other methods of monitoring the water remaining in monitoring well 300 could be used, with an exemplary method described hereinafter.

Housing 301 defines a cavity 314 as illustrated in FIG. 4. From this fragmentary view, a receptacle 340 is illustrated and which is proximately located beneath the reservoir 310. The receptacle 340 includes a first portion 341 which is located within cavity 314, and a second portion 342 which extends laterally from the left surface 304 of housing 301. The first portion 341 comprises a material impervious to water, for example, plastic, polyvinyl chloride (PVC) or stainless steel. The second portion 342 comprises a material, for example, porous ceramic, with a porous configuration that allows water to freely flow across the second portion 342 while restricting the flow of air. Such porous configuration is understood in the art.

First and second portions 341 and 342 of the receptacle 340 define a fluid chamber 350. The first portion 341 has an upper section 343 which is located proximate the reservoir 310, and an opposite lower section 344. The upper section 343 defines a frustoconical shaped aperture 345 which provides fluid communication between the reservoir 310 and the fluid chamber 350 of receptacle 340. The frustoconical shape of the aperture 345 is designed to complement the frustoconical shape of the resilient sealing member 317 such that receipt of the resilient sealing member 317 in the aperture 345 fluidly seals the fluid chamber 350 from the reservoir 310.

The lower section 344 has a tube 346, or conduit, which extends downwardly from the lower section 344 and which fluidly connects to a geophysical monitoring device 347 to provide fluid communication between the fluid chamber 350 of the receptacle 340 and the geophysical monitoring device 347. In particular, the geophysical monitoring device 347 is disposed in sensing relation relative to the fluid chamber 350 of receptacle 340 by way of conduit 346. An exemplary geophysical monitoring device 347 includes a pressure transducer as noted earlier. As seen in FIG. 4, the second portion 342 of receptacle 340 has a concave porous surface 348 to provide hydraulic contact with below-grade earthen soil. This is best shown in FIG. 6.

Still referring to FIG. 4, monitoring well 300 includes electrical components, for example, a microcontroller, or intelligent controller 360; a data transmission circuitry 370; and electrical storage device 380 secured within cavity 314 of housing 301. These assemblies are operatively, or electrically, coupled by a plurality of conductors 316 as understood by one skilled in the art. Only as an example, and with it understood that other arrangements are possible, the microcontroller 360 is positioned below the geophysical monitoring device 347; the data transmission circuitry 370 is positioned below the microcontroller 360; and the electrical storage device 380 is positioned below the data transmission circuitry 370 and just above the bottom surface 306 of housing 301. An exemplary electrical storage device 380 includes a battery. This battery could be of a rechargeable or non-rechargeable type.

FIG. 5 best illustrates the cooperation between the resilient sealing member 317 and the aperture 345 of receptacle 340. In preparing the monitoring well 300 for operation, the resilient sealing member 317 is positioned away from the aperture 345 to provide fluid communication between the reservoir 310 and the fluid chamber 350 of receptacle 340. As should be understood, water 385 is provided within the reservoir 310 through aperture 308 (FIG. 4) and flows under the influence of gravity into the fluid chamber 350 through aperture 345. The water in the fluid chamber 350 is represented by numeral 386. The fluid chamber 350 is normally completely filled with water 386. However, it is possible that degassed water may be used to fill the reservoir 310 and fluid chamber 350. The reservoir 310 may be provided with water 385 to any level desired. However, the more water 385 provided, the less frequently field maintenance of the monitoring well 300 needs to be performed. This field maintenance may include, for example, removing air from the fluid chamber 350. This alleviates a significant expense of using monitoring wells in field applications.

After providing the water, the actuator (an exemplary actuator is shown in FIGS. 2–3) is energized to move the drive arm 315 downwardly to drive or otherwise place the resilient sealing member 317 into occluding relation relative to the aperture 345. As will be seen, the frustoconical shape of the resilient sealing member 310 complements the frustoconical shape of the aperture 345 for fluidly sealing receipt therein and selectively impedes fluid communication between the reservoir 310 and the receptacle 340. As best seen in FIG. 6, the monitoring well 300 is positioned within the below-grade earthen soil 336 with the receptacle 340 in hydraulic contact with the soil 336. Referring now to FIG. 5, the water in the fluid chamber 350 is pulled through the concave porous surface 348 of receptacle 340 thus creating a pocket of trapped air 387 which will form at the elevationally highest portion of the receptacle 340, and in this embodiment, is proximately located relative to the aperture 345. As explained in the Background section (above), the presence of air is undesirable because accurate measurements of relative soil moisture are difficult to obtain under these circumstances. Accordingly, the actuator is energized from time-to-time to move the drive arm 315 upwardly to remove the resilient sealing member 317 from its occluding relationship relative to the aperture 345. When this is achieved, fluid communication between fluid chamber 350 and reservoir 310 is established. Water 385 from reservoir 310 flows under these circumstances into fluid chamber 350 to fill same and displaces the pocket of trapped air 387 as air bubbles 388 to travel or move into the reservoir 310.

Referring now to FIG. 6, monitoring well 300 is shown in hydraulic contact with the below-grade earthen soil 336 with antenna 313 extending from housing 301 and which is located at least partially above-grade of the earthen soil 336. Data transmission circuitry 370 is sealed within the cavity 314 of housing 301 (shown in FIG. 4) and operably couples the antenna 313 to the pressure transducer 307. Data generated by the pressure transducer 347 (shown in FIG. 4) is transmitted to a remote location (not shown) by way of, for example, radio waves 390.

It should be understood that data storage and transmission could be accomplished with the monitoring well 300 being electrically coupled to a data logging device or controller similar to that illustrated in FIG. 1. Additionally, it should be understood that data transmitted from the pressure transducer 307 could include information regarding the water remaining in receptacle 340 by calibrating the pressure of the remaining water above the pressure transducer 307 and assigning a value to that pressure value. The pressure value is then processed by comparing the pressure value to a threshold value whereupon once the pressure value drops below or at the threshold value, further processing occurs to ultimately signal the actuator to be energized wherein the resilient sealing member 317 is moved from aperture 345 to allow water to flow into the fluid chamber 350 from reservoir 310. Accordingly, the receptacle 340 can be periodically filled with water automatically without the significant expense of field personnel having to physically access the monitoring well 300 to determine the water remaining.

Figure 8:
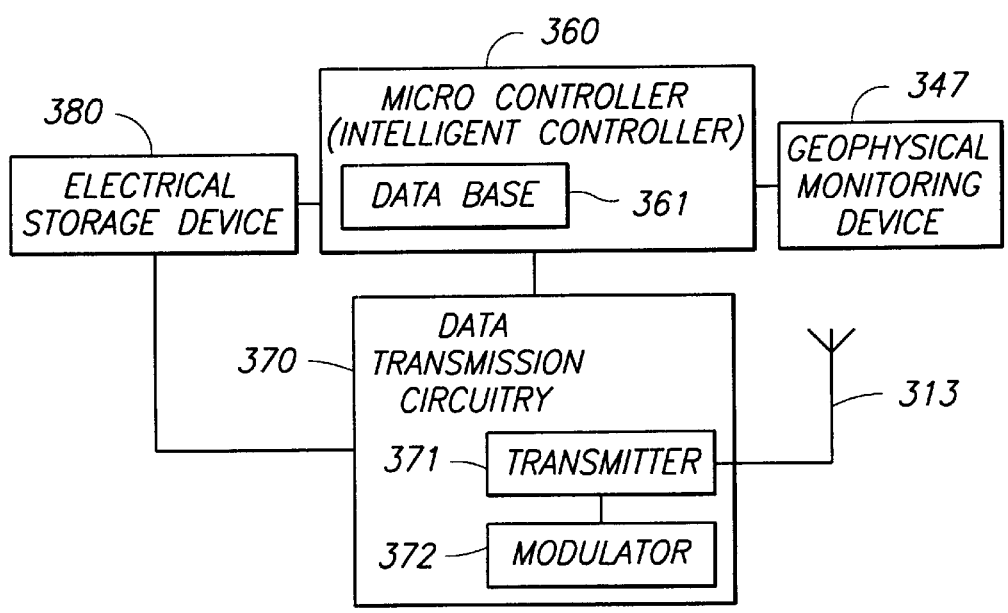
FIG. 8 is a block diagram of data transmission circuitry coupled to a rechargeable battery, geophysical monitoring device and microcontroller of the present invention.

Referring now to FIG. 8, exemplary data transmission circuitry 370 is illustrated and comprises a transmitter 371; and a modulator 372. It should be understood that the data transmission circuitry 370 is operatively coupled in signal receiving and transmitting relation relative to the antenna 313. Data transmission circuitry 370 is operatively coupled to each of the microcontroller 340; the geophysical monitoring device 347; and the electrical storage device 380. As earlier noted, the microcontroller 360 includes a database 361 and is operatively coupled to the data transmission circuitry 370 and pressure transducer 347. The electrical storage device 380 is operatively coupled to the microcontroller 360 and data transmission circuitry 370.

The operation of the described embodiments of the present invention are believed to be readily apparent and are briefly summarized at this point.

The monitoring well 300 includes a housing 301 which defines a cavity 314. The housing 301 is buried in an earthen soil 336 location below-grade and the cavity 314 is sealed from the environment. The housing 301 defines a reservoir 310 within the cavity 314 which is fluidly sealed from the cavity 314, and wherein the reservoir 310 encloses a source of water 385. A porous receptacle 340 is borne by the housing 301 and the porous receptacle 340 defines a fluid chamber 350 filled with water 386 such that the porous receptacle 340 is in hydraulic contact with the below-grade earthen soil 336. A pressure transducer 347 is disposed in sensing relation relative to the fluid chamber 350 of the porous receptacle 340.

An aperture 345 is defined by the housing 301 to provide fluid communication between the reservoir 310 and the fluid chamber 350 of the porous receptacle 340, and the aperture 345 has a substantially frustoconical shape.

An actuator 200 is provided and which includes a driving device, for example, a motor 201, and a drive member 315 disposed in force receiving relation relative the driving device 201. A resilient sealing member 317 has a frustoconical shape which complements the aperture 345 for fluidly sealing receipt therein, and which is mounted on the drive member 315. Energizing the driving device 201 causes the sealing member 317 to selectively obstruct and permit fluid communication between the reservoir 310 and porous receptacle 340. During the fluid communication, water from the reservoir 310 flows into the fluid chamber 350 of the porous receptacle 340.

An antenna 313 extends from the housing 301 and is located at least partially above-grade of the earthen soil 336. Data transmission circuitry 370 is sealed within the cavity 314 and operatively couples the antenna 313 to the pressure transducer 347. Data generated by the pressure transducer 347 is transmitted to a remote location.

A microcontroller 360 is operatively coupled to the data transmission circuitry 370 and pressure transducer 347. An electrical storage device 380 is operatively coupled to the microcontroller 360 and data transmission circuitry 370.

An exemplary actuator 200 of the present invention includes a motor 201; a drive member 209; and gear structures which include a drive shaft 202, pinion 203 and gear 204; and wherein the gear structures are operatively coupled between the motor 201 and the drive member 209. The drive member 209 is disposed in force receiving relation relative the motor 201. Furthermore, the drive member 209 has a terminal end 215. Energizing the motor 201 causes the substantially reciprocal movement of the terminal end 215 of the drive member 209 such that the terminal end 215 selectively inhibits fluid communication between the porous receptacle 60, or housing, and the cavity 27.

Another exemplary embodiment of the monitoring well 10 comprises a conduit 20 which defines a passageway 27 having at least one outlet 26. The conduit 20 is substantially linear and has opposite proximal and distal ends 21 and 22, respectively, and wherein the proximal end 21 of the conduit 20 is located in an earthen soil 12 location above-grade 11, and the distal end 22 of the conduit 20 is buried in the earthen soil location below-grade 12. The outlet is defined by a frustoconically shaped surface 26 formed in the distal end 22 with an inside diametral dimension 25 which has a largest diametral dimension of the frustoconically shaped surface 26 located in spaced relation relative to the distal end 22, and the smallest diametral dimension of the frustoconical surface 26 located adjacent the distal end 22.

A porous housing or receptacle 60 is borne by the conduit 20, and the porous housing 60 defines a fluid chamber 65 which is disposed in fluid communication with the passageway 27 by way of the outlet 26.

A geophysical monitoring device 100 is received in the passageway 27 of the conduit 20 and is coupled in sensing relation relative to the fluid chamber 65 of the porous housing 60.

A coupler 83, or sealing member, is movably mounted in the passageway 27 and which selectively couples the porous housing fluid chamber 65 in fluid flowing relation relative to the passageway 27 defined by the conduit 20. An actuator 80 is coupled in force transmitting relation relative to the coupler 83 to selectively position the coupler 83 in a position to allow fluid communication between the passageway 27 defined by the conduit 20, and fluid chamber 65 defined by the porous housing 60.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

We claim:

1. A monitoring apparatus, comprising:

a housing defining a cavity;

a porous receptacle borne by the housing, the porous receptacle defining a fluid chamber disposed in fluid communication with the cavity;

a geophysical monitoring device disposed in sensing relation relative to the fluid chamber of the porous receptacle; and a linear actuator for selectively inhibiting fluid communication between the porous receptacle and cavity.

2. A monitoring apparatus as claimed in claim 1, and further comprising:

an antenna extending from the housing; and data transmission circuitry operatively coupling the antenna to the geophysical monitoring device, and wherein data generated by the geophysical monitoring device is transmitted by the antenna to a remote location.

3. A monitoring apparatus as claimed in claim 2, wherein the data transmission circuitry is sealed within the cavity.

4. A monitoring apparatus as claimed in claim 2, wherein the data transmission circuitry comprises a modulator operatively coupled to the geophysical monitoring device, and a transmitter operatively coupled to the modulator and antenna.

5. A monitoring apparatus as claimed in claim 2, and further comprising:

a microcontroller operatively coupled to each of the geophysical monitoring device, the data transmission circuitry, and the actuator; and an electrical storage device operatively coupled to the microcontroller and data transmission circuitry.

6. A monitoring apparatus as claimed in claim 5, wherein the electrical storage device comprises a rechargeable battery.

7. A monitoring apparatus as claimed in claim 2, wherein the antenna is located in an earthen soil location at least partially above grade, and wherein the housing is buried at least in part in an earthen soil location below-grade.

8. A monitoring apparatus as claimed in claim 2, wherein the modulator comprises a frequency modulator.

9. A monitoring apparatus as claimed in claim 1, wherein the actuator comprises a solenoid.

10. A monitoring apparatus as claimed in claim 1, wherein the housing comprises a reservoir in fluid communication with the cavity.

11. A monitoring apparatus as claimed in claim 1, wherein the geophysical monitoring device comprises a pressure transducer operatively coupled to the porous receptacle.

12. A monitoring apparatus as claimed in claim 11, wherein the housing seals the transducer and actuator from the environment.

13. A monitoring apparatus as claimed in claim 1, and further comprising a controller electrically coupled to the geophysical monitoring device and electrically coupled to the actuator, and wherein the controller actuates the actuator at predetermined time intervals.

14. A monitoring apparatus as claimed in claim 1, and further comprising a controller electrically coupled to the geophysical monitoring device and electrically coupled to the actuator, and wherein the controller comprises a memory defining a database; a microprocessor electrically coupled to the memory; and an output device electrically coupled to the microprocessor.

15. A monitoring apparatus as claimed in claim 1, and further comprising a controller electrically coupled to the geophysical monitoring device and electrically coupled to the actuator, and wherein the controller actuates the actuator when the geophysical monitoring device senses a predetermined geophysical value being monitored.

16. A monitoring apparatus as claimed in claim 1, and further comprising:

an aperture defined by the housing and which provides fluid communication between the porous receptacle and the cavity; and a sealing member disposed in force receiving relation relative the actuator, and wherein the actuator selectively moves the sealing member along a path of travel between a first position and a second position.

17. A monitoring apparatus as claimed in claim 16, wherein the sealing member comprises resilient material.

18. A monitoring apparatus as claimed in claim 16, wherein the sealing member comprises a polymeric-based material.

19. A monitoring apparatus as claimed in claim 16, wherein the sealing member when located in the first position substantially occludes the aperture to impede fluid communication between the porous receptacle and the cavity, and wherein the sealing member when located in the second position is positioned remotely relative to the aperture and provides fluid communication between the porous receptacle and the cavity.

20. A monitoring apparatus as claimed in claim 19, and further comprising a reservoir borne by the housing and which stores water, and wherein the reservoir is disposed in fluid communication with the fluid chamber of the porous receptacle by way of the aperture, and wherein the sealing member when disposed in the second position allows the water from the reservoir to flow into the fluid chamber.

21. A monitoring apparatus as claimed in claim 16 wherein the aperture is defined by an inside diametral dimension that diminishes when measured in the direction extending from the cavity to the porous receptacle, and wherein the sealing member comprises a frustoconical-shaped resilient member.

22. A monitoring apparatus as claimed in claim 19, and further comprising a substantially linear arm having a proximal end and an opposite, distal end, the arm slidingly supported by the housing for substantially reciprocal movement within the cavity, and wherein the actuator is mounted in force transmitting relation relative to the proximal end of the arm and the sealing member is mounted in force receiving relation relative the distal end of the arm.

23. A monitoring apparatus as claimed in claim 1, and wherein the actuator comprises a motor; a drive member; and gear structures; and wherein the gear structures are operatively coupled between the motor and the drive member, and wherein the drive member is disposed in force receiving relation relative the motor, and wherein the drive member has a terminal end, and wherein energizing the motor causes the substantially reciprocal movement of the terminal end of the drive member and wherein the movement of the terminal end selectively inhibits fluid communication between the porous receptacle and the cavity.

24. A monitoring apparatus as claimed in claim 23, wherein the drive member includes first and second members disposed in telescoping relation relative to each other, and wherein the drive member further comprises a biasing member operatively coupled between the respective members to bias each apart.

25. A monitoring apparatus as claimed in claim 24, wherein the biasing member comprises a spring.

26. A monitoring well, comprising:

a housing defining a cavity, wherein the housing is buried in an earthen soil location below-grade and the cavity is sealed from the environment, and the housing defining a reservoir within the cavity which is fluidly sealed from the cavity, and wherein the reservoir encloses a source of water;

a porous receptacle borne by the housing, the porous receptacle defining a fluid chamber filled with water, and wherein the porous receptacle is in hydraulic contact with the below-grade earthen soil;

a pressure transducer disposed in sensing relation relative to the fluid chamber of the porous receptacle;

an aperture defined by the housing to provide fluid communication between the reservoir and the fluid chamber of the porous receptacle, the aperture having a substantially frustoconical shape; and an actuator comprising a driving device, a drive member disposed in force receiving relation relative the motor, and a resilient sealing member having a frustoconical shape which complements the aperture for fluidly sealing receipt therein, and which is mounted on the drive member, and wherein energizing the driving device causes the sealing member to selectively obstruct and permit fluid communication between the reservoir and porous receptacle, and wherein during the fluid communication, water from the reservoir flows into the fluid chamber of the porous receptacle.

27. A monitoring well, comprising:

a housing defining a cavity, wherein the housing is buried in an earthen soil location below-grade and the cavity is sealed from the environment, and the housing defining a reservoir within the cavity which is fluidly sealed from the cavity, and wherein the reservoir encloses a source of water;

a porous receptacle borne by the housing, the porous receptacle defining a fluid chamber filled with water, and wherein the porous receptacle is in hydraulic contact with the below-grade earthen soil;

a pressure transducer disposed in sensing relation relative to the fluid chamber of the porous receptacle;

an aperture defined by the housing to provide fluid communication between the reservoir and the fluid chamber of the porous receptacle, the aperture having a substantially frustoconical shape; and an actuator comprising a driving device, a drive member disposed in force receiving relation relative the driving device, and a resilient sealing member having a frustoconical shape which complements the aperture for fluidly sealing receipt therein, and which is mounted on the drive member, and wherein energizing the driving device causes the sealing member to selectively obstruct and permit fluid communication between the reservoir and porous receptacle, and wherein during the fluid communication, water from the reservoir flows into the fluid chamber of the porous receptacle;

an antenna extending from the housing and which is located at least partially above grade of the earthen soil;

data transmission circuitry sealed within the cavity and operatively coupling the antenna to the pressure transducer, and wherein data generated by the pressure transducer is transmitted to a remote location;

a microcontroller operatively coupled to the data transmission circuitry and pressure transducer; and an electrical storage device operatively coupled to the microcontroller and data transmission circuitry.

* * * * *